United States Patent
Stockton et al.

(10) Patent No.: US 10,182,336 B1
(45) Date of Patent: Jan. 15, 2019

(54) LOW POWER ADVERTISEMENT SCHEDULE FOR IMPLANTABLE MEDICAL DEVICE AND METHOD

(71) Applicant: PACESETTER, INC., Sylmar, CA (US)

(72) Inventors: John Stockton, Chartsworth, CA (US); Perry Li, Arcadia, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 15/845,878

(22) Filed: Dec. 18, 2017

(51) Int. Cl.
| | |
|---|---|
| *H04W 8/00* | (2009.01) |
| *H04W 52/32* | (2009.01) |
| *A61N 1/36* | (2006.01) |
| *H04W 52/38* | (2009.01) |
| *H04W 76/14* | (2018.01) |
| *A61N 1/372* | (2006.01) |

(52) U.S. Cl.
CPC ........ *H04W 8/005* (2013.01); *A61N 1/36125* (2013.01); *A61N 1/37264* (2013.01); *H04W 52/325* (2013.01); *H04W 52/383* (2013.01); *H04W 76/14* (2018.02); *A61N 1/37235* (2013.01)

(58) Field of Classification Search
CPC ... H04W 8/005; H04W 76/14; H04W 52/383; H04W 52/325
USPC ........................................... 455/41.2
See application file for complete search history.

(56) References Cited

U.S. PATENT DOCUMENTS

| | | | |
|---|---|---|---|
| 2006/0020300 A1* | 1/2006 | Nghiem | A61B 5/0031 607/60 |
| 2014/0169162 A1* | 6/2014 | Romano | H04L 47/25 370/230 |

* cited by examiner

*Primary Examiner* — Ayodeji Ayotunde

(57) ABSTRACT

Methods and devices are provided for managing establishment of a communications link between an external instrument (EI) and an implantable medical device (IMD). The method stores, in the IMD, an advertisement schedule that includes first and second power schemes to be utilized with advertisement notices. The first and second power schemes define at least one of i) first and second power levels for transmitting the advertisement notices or ii) first and second receive sensitivities to scan for a connection request. The method manages at least one of a transmit or receive operation of the IMD, utilizing the first and second power schemes in connection with first and second advertisement notices, respectively. The method establishes a communication session between the IMD and the EI.

20 Claims, 6 Drawing Sheets

LOW POWER ADVERTISEMENT SCHEDULE FOR IMPLANTABLE MEDICAL DEVICE AND METHOD

BACKGROUND

An implantable medical device (IMD) is a medical device that is configured to be implanted within a patient anatomy and commonly employs one or more leads with electrodes that either receive or deliver voltage, current or other electromagnetic pulses from or to an organ or tissue for diagnostic or therapeutic purposes. In general, IMDs include a battery, electronic circuitry, a pulse generator, a transceiver and/or a microprocessor that is configured to handle communication with an external instrument as well as control patient therapy. The components of the IMD are hermetically sealed within a metal housing.

IMDs are generally programmed by, and exchange data with, external instruments controlled by physicians and/or the patient. Some commercially available external instruments use commercial operating systems (e.g., iOS, Android) that communicate through wireless bi-directional communication links with the IMDs. For example, mobile devices with Bluetooth Low Energy (BLE) circuitry are available for communication with certain implantable medical devices. The bi-direction communication links are formed using a wireless communication protocol that includes advertisement notices received by the external instruments. The advertisement notices are broadcast by the IMD at predetermined constant frequencies. The use of the advertising notices to facilitate the establishment of wireless communications involves a significant power consumption for the implanted medical device.

Currently, a strategy for connecting to a BLE enabled IMD is for the IMD to periodically advertise for a duration of the IMD life. Unfortunately, for IMDs with smaller batteries, the advertisement notices are spaced far apart over long advertisement intervals (e.g., minutes) in order to save battery life and extend longevity. In addition, it has been proposed, to use another external device such as a magnet to initiate a fast advertisement state in the IMD. The drawback of using a magnet is that the magnet introduces the inconvenience of having to carry extra external hardware. Also, a magnet can be used to change the behavior of the implantable device, and thus unintended consequences are possible.

BRIEF SUMMARY

In accordance with embodiments herein, a method is provided for managing establishment of a communications link between an external instrument (EI) and an implantable medical device (IMD). The method stores, in the IMD, an advertisement schedule that includes first and second power schemes to be utilized with advertisement notices. The first and second power schemes define at least one of i) first and second power levels for transmitting the advertisement notices or ii) first and second receive sensitivities to scan for a connection request. The method manages at least one of a transmit or receive operation of the IMD, utilizing the first and second power schemes in connection with first and second advertisement notices, respectively. The method establishes a communication session between the IMD and the EI.

Optionally, the first power scheme may define a short range advertisement scheme having a first transmit power level and a first receive sensitivity configured to communicate with an external device up to 1 meter from the IMD. The first transmit power level may be no more than −5 dBm. The second power scheme may define a long range advertisement schedule having a second transmit power level and a second receive sensitivity that may be configured to communicate with an external device that may be great than 1 meter away from the IMD. The second transmit power level and second receive sensitivity may be configured to communicate with an external device that is up to 5 meters away from the IMD. The second transmit power level may be at least 3 dBm.

Optionally, the advertisement schedule may repeat the first power scheme N times before repeating the second power scheme, where N is greater than or equal to 1. The first and second power schemes may correspond to short and long range advertisement schemes. The advertisement schedule may merge the short and long range advertisement schemes in a ratio LR/SR of no more than 50.0%, where LR may correspond to a number of long range advertisement complexes transmitted during a predetermined period of time and SR corresponds to a number of short range advertisement complexes transmitted during the predetermined period of time. The method may count a number of unsuccessful advertisement states and based thereon, change from the first power scheme. The method may determine when a connection request is received from the EI in connection with one of the advertisement notices.

In accordance with embodiments herein, an implantable medical device (IMD) is provided. The IMD comprises memory storing an advertisement schedule that includes first and second power schemes to be utilized with advertisement notices. The first and second power schemes define at least one of i) first and second power levels for transmitting the advertisement notices or ii) first and second receive sensitivities to scan for a connection request. A transmitter is configured to transmit the advertisement notices. A receiver is configured to sense for the connection request. A processor is configured to manage at least one of the transmitter or receiver utilizing the first and second power schemes in connection with first and second advertisement notices, respectively and to establish a communications link between the IMD and an external instrument (EI).

Optionally, based on the first power scheme, the processor may be configured to define a short range advertisement scheme that may have a first transmit power level and a first receive sensitivity configured to communicate with an external device up to 1 meter from the IMD. The processor may be configured to set the first transmit power level of the transmitter to no more than −5 dBm. Based on the second power scheme, the processor may be configured to define a long range advertisement scheme having a second transmit power level and a second receive sensitivity configured to communicate with an external device that may be great than 1 meter away from the IMD. The processor may be configured to set the second transmit power level and second receive sensitivity to communicate with an external device that is up to 5 meters away from the IMD.

Optionally, the processor may be configured to set the second transmit power level to at least 3 dBm. Based on the advertisement schedule, the processor may be configured to repeat the first power scheme N times before repeating the second power scheme, where N is greater than 1. The first and second power schemes may correspond to short and long range advertisement schemes. The advertisement schedule may merge the short and long range advertisement schemes in a ratio LR/SR of no more than 50.0%, where LR corresponds to a number of long range advertisement complexes transmitted during a predetermined period of time and SR corresponds to a number of short range advertisement complexes transmitted during the predetermined period of time. The processor may be further configured to count a number of unsuccessful advertisement states and based thereon, change to another power scheme. The processor may be further configured to determine when a connection request is received from the EI in connection with one of the advertisement notices.

DETAILED DESCRIPTION

Figure 1:
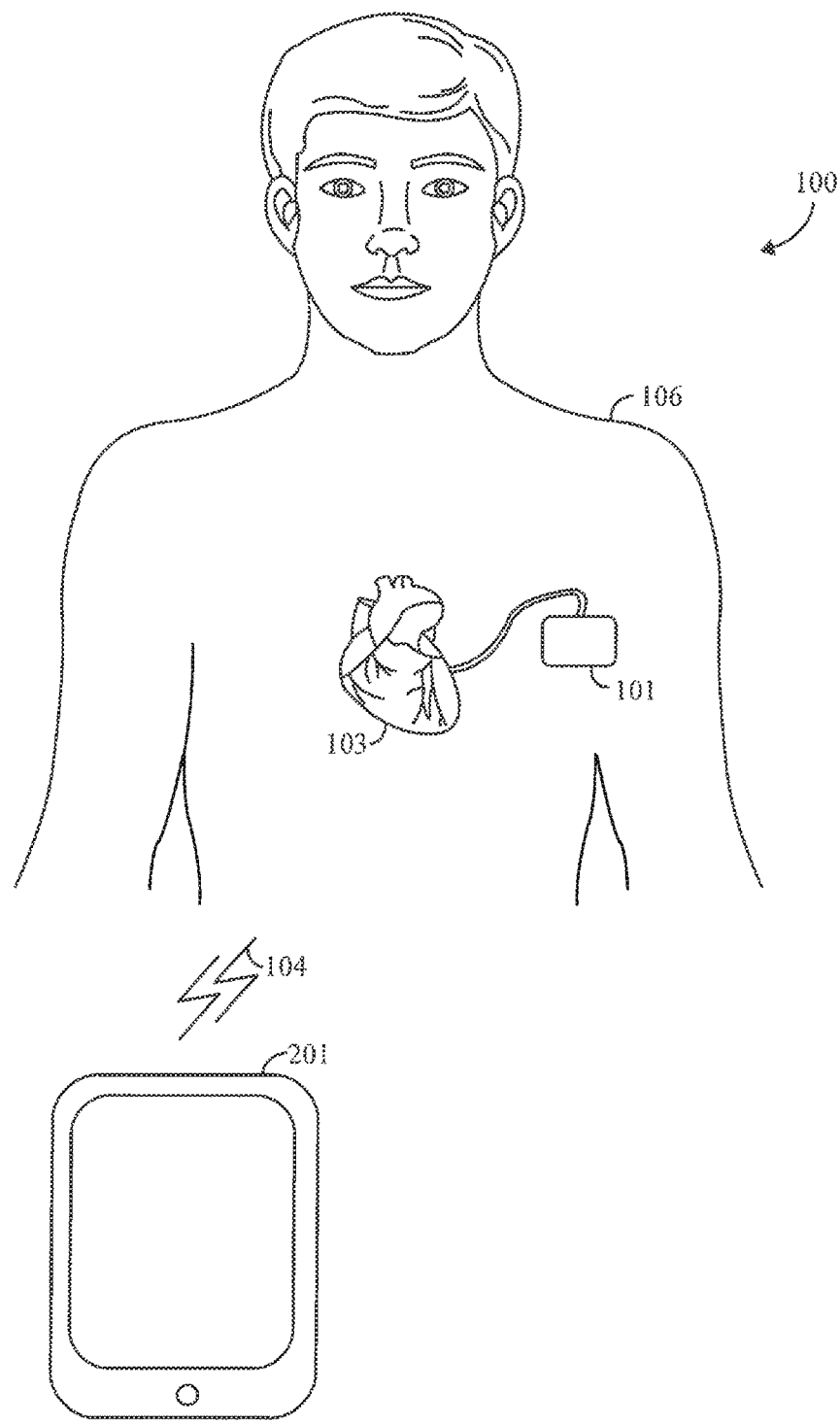
FIG. 1 illustrates a simplified block diagram of a system for initiating a bi-directional communication link in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Various embodiments described herein include a method and/or system to manage advertisement and scanning schedules utilized in connection with establishing a wireless bi-directional communication link between an implantable medical device (IMD) and an external instrument (EI). A technical effect of embodiments herein provides a new advertisement schedule that manages power usage and a frequency of advertisement pulses transmitted from a BLE transceiver in the implantable medical device. Embodiments herein overcome difficulties of current advertisement schedules, in which the BLE transceiver transmits all advertisement pulses at a common single power level that is set to afford a maximum communications range (e.g., for external devices that are several feet from the IMD). Conventional advertisement schedules set the power level at or near a maximum IMD output power level for all advertisement notices. Conventional advertisement schedules do not adequately balance strict battery requirements for IMDs by managing the transceiver average current consumption versus unduly large advertisement intervals. Overly large advertisement intervals translate to longer delays before a connection is established (e.g., advertisement on the order of every 10's of seconds).

A technical effect of embodiments herein addresses the foregoing concerns by providing a new advertisement schedule that transmits advertisement pulses with different power levels and/or adjusts receive sensitivity, alone or in combination with changes in the advertisement interval. The new advertisement schedule varies output power and/or receive sensitivity to better suit use cases and extend IMD longevity. For example, the new advertisement schedule uses a relatively low power level, such as the lowest power available, during short advertisement intervals and uses a relatively high power level during longer advertisement intervals. In some embodiments, the power level is adjusted for both transmit operations (e.g., transmitting an advertisement pulse) and receive operations (e.g., when listening for a response from an external device).

In accordance with embodiments herein, two common use cases are patient initiated connect-on-demand (COD) and automatic remote monitoring. During patient initiated COD, the patient will seek to initiate communication through a handheld external device (e.g., smart phone), while holding the external device at a distance up to an arm length away from the body. It is desirable that the external device connect to the IMD as soon as practical, such as to allow IMD changes or triggering of events without the patient waiting an unnecessarily long period of time. For patient initiated COD, lower transmit power and receive sensitivity can be used because the communication distance is short (e.g., no more than 3-4 feet). The lower transmit and receive settings assist in conserving current consumption which can then be used to support a faster advertisement rate (e.g., shorter advertisement interval or period). A faster advertisement rate reduces connection delay while maintaining the desired implant longevity which results in an improved user experience. The foregoing type of advertisement mode is referred to as short range advertisement.

During remote monitoring, an external device (e.g., smart phone or bedside monitor) automatically attempts to communicate with the IMD periodically (e.g., once per day). During remote monitoring, the IMD may be farther away (e.g., over 3-4 feet) from the external device such as when the patient is sleeping and the external device is in another part of the room. As the external device automatically attempts to connect without patient interaction, the connection delay is less of interest because the patient is not waiting for a connection. During remote monitoring, higher transmit power and increased receive sensitivity, relative to short range advertisement, are utilized in order to extend the communication range. The higher transmit power and receive sensitivity result in higher current consumption, and accordingly, embodiments herein, reduce the advertisement rate (e.g., increase the advertisement interval or period) in order to maintain implant longevity. As remote monitoring normally occurs automatically with the patient unaware, the patient would not experience the slower connection time. The foregoing type of advertisement mode is referred to as long range advertisement.

FIG. 1 illustrates a simplified block diagram of a system 100 for initiating a bi-directional communication link. The system 100 includes an IMD 101 and an EI 201 (e.g., table computer, smart phone, smart watch, laptop, and/or the like), according to an embodiment. The IMD 101 may be implanted within a patient 106 (e.g., proximate to and/or within a heart 103, proximate to the spinal cord). Additionally or alternatively, the IMD 101 may have components that are external to the patient. For example, the IMD 101 may include an external pulse generator (EPG). Optionally, the IMD 101 may be one of various types of implantable devices, such as, for example, an implantable cardiac recorder, a neurostimulator, an implantable pacemaker, implantable cardioverter-defibrillator (ICD), defibrillator, cardiac rhythm management (CRM) device, an implantable pulse generator (IPG), or the like.

Optionally, the IMD 101 may be a leadless pacer, examples of which are disclosed in U.S. Pat. No. 9,072,913, entitled, "RATE RESPONSIVE LEADLESS CARDIAC PACEMAKER," and U.S. Pat. No. 9,168,383, entitled "LEADLESS CARDIAC PACEMAKER WITH CONDUCTED COMMUNICATION," METHOD OF FABRICATING STIMULATION LEAD FOR APPLYING ELECTRICAL STIMULATION TO TISSUE OF A PATIENT," which are expressly incorporated herein by reference. Additionally or alternatively, the IMD 101 may be a leadless monitor, examples of which are disclosed in U.S. patent application Ser. No. 15/084,3793, filed Mar. 26, 2016 entitled, "METHOD AND SYSTEM TO DISCRIMINATE RHYTHM PATTERNS IN CARDIAC ACTIVITY," which is expressly incorporated herein by reference.

The EI 201 is configured to establish a wireless bi-directional communication link 104 with the IMD 101. The communication link 104 allows the EI 201 to receive measurements from the LMD 101, and to program or send instructions to the IMD 101. The communication link 104 may use a standard wireless protocol such as Bluetooth Low Energy, Bluetooth, Medical Implant Communication Service, and/or the like. The EI 201 may be located within a home of the patient 106, a hospital, an automobile, at an office of the patient 106, or the like.

Figure 2:
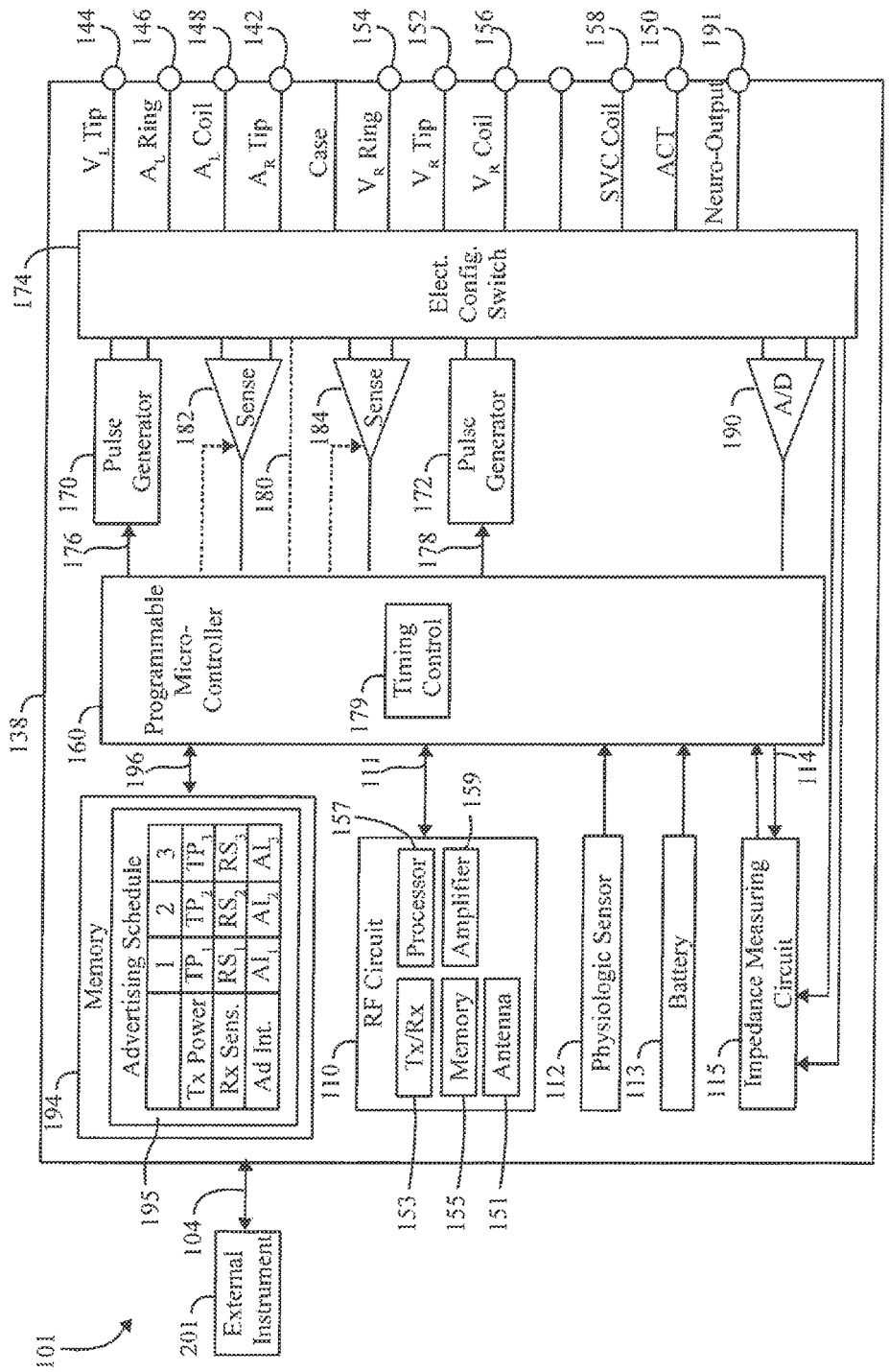
FIG. 2 illustrates a block diagram of internal components of the IMD in accordance with embodiments herein.

FIG. 2 illustrates a block diagram of internal components of the IMD 101. The components described herein can include or represent hardware and software instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. Additionally or alternatively, the components may be hard-wired logic circuits.

The IMD 101 is for illustration purposes only, and it is understood that the circuitry could be duplicated, eliminated or disabled in any desired combination to provide a device capable of treating the appropriate heart chamber(s) with cardioversion, defibrillation and/or pacing stimulation as well as providing for apnea detection and therapy. Additionally or alternatively, the IMD 101 may be used to generate neurostimulation for application to a desired area of a body, such as spinal cord stimulation, the brain and the like.

The housing 138 for the IMD 101, shown schematically in FIG. 2, is often referred to as the "can", "case" or "case electrode" and may be programmably selected to act as the return electrode for all "unipolar" modes. The housing 138 may further be used as a return electrode alone or in combination with one or more of the coil electrodes for shocking purposes. The housing 138 further includes a connector (not shown) having a plurality of terminals. The terminals may be configured to be coupled to different types of electrodes and leads. All or a portion of the terminals may be used in various combinations. It is recognized that alternative types of electrodes may be utilized in place of, or in addition to, the examples of FIG. 2. The following examples are provided as non-limiting examples of terminals: 142 (right atrial tip electrode), 144 (left ventricular tip electrode), 146 (left atrial ring electrode), 148 (left atrial coil electrode), 150 (acoustical terminal, ACT electrode), 152 (ventricular tip electrode), 154 (right ventricular ring electrode), 156 (right ventricular coil electrode), and 158 (superior vena cava coil electrode). In addition, a terminal 191 is indicated to be representative of one or more neural stimulation electrodes that may be utilized in place of or in addition to the above noted electrodes.

The IMD 101 includes a controller circuit 160 which controls operation of the IMD 101. The controller circuit 160 (also referred to herein as a processor module or unit) may include one or more processors, or equivalent control circuitry, designed specifically for controlling the delivery of stimulation therapy and may further include RAM or ROM memory, logic and timing circuitry, state machine circuitry, and I/O circuitry. Typically, the controller circuit 160 includes the ability to process or monitor input signals (data) as controlled by program code stored in memory. The details of the design and operation of the controller circuit 160 are not critical to the invention. Rather, any suitable controller circuit 160 may be used that carries out the functions described herein. Among other things, the controller circuit 160 receives, processes, and manages storage of digitized cardiac data sets from the various sensors and electrodes. For example, the cardiac data sets may include IEGM data, pressure data, heart sound data, and the like.

The IMD 101 includes pulse generators 170, 172 to generate stimulation pulses for delivery by one or more leads and/or electrodes. The stimulation may be configured in different manners, such as in connection with neural stimulation, pacing pulse stimulation, cardioversion stimulation, defibrillation shocks, and the like. The pulse generators, 170 and 172, may include dedicated, independent pulse generators, multiplexed pulse generators or shared pulse generators. The pulse generators, 170 and 172, are controlled by the controller circuit 160 via appropriate control signals, 176 and 178, respectively, to trigger or inhibit the stimulation pulses.

The pulse generators 170, 172 may be represent atrial and/or ventricular pulse generators, where the stimulation pulses are delivered through a plurality of electrodes and/or leads located within or proximate to the heart. Optionally, the pulse generators 170, 172 may represent neurostimulation pulse generators to generate stimulation pulses for a brain or spinal cord nervous system. The stimulation pulses are delivered by a plurality of electrodes through the neuro output lead 191. The neuro stimulation pulse generator circuit is controlled by the controller circuit 160 via appropriate control signals to trigger or generate the stimulation pulses.

The controller circuit 160 further includes timing control circuitry 179 used to control the timing of such stimulation pulses (e.g., the neural stimulation waveforms, pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 174 includes a plurality of switches for connecting the desired electrodes to the appropriate I/O circuits, thereby providing complete electrode programmability. Accordingly, the switch 174, in response to a control signal 180 from the controller circuit 160, determines the polarity of the stimulation pulses (e.g., unipolar, bipolar, etc.) by selectively closing the appropriate combination of switches (not shown).

A sensing circuit 182 and sensing circuit 184 may also be selectively coupled to one or more leads through the switch 174 for collecting sensed physiologic data (e.g., cardiac activity, neural activity, respiratory activity, etc.). The sensing circuits, 182 and 184, may include dedicated sense amplifiers, multiplexed amplifiers or shared amplifiers. The outputs of the sensing circuits, 182 and 184, are connected to the controller circuit 160 which, in turn, receives the sensed data and is able to trigger or inhibit the pulse generators, 170 and 172, respectively, in a demand fashion in response to the absence or presence of activity of interest.

Sensed signals are also applied to the inputs of an analog-to-digital (A/D) data acquisition system 190. The data acquisition system 190 is configured to acquire IEGM signals, neural signals, and the like. The data acquisition system 190 converts the raw analog data into a digital signal, and stores the digital signals in memory 194 for later processing and/or RF transmission to the EI 201. The data acquisition system 190 is coupled to one or more leads through the switch 174 to sample signals across any combination of desired electrodes. The data acquisition system 190 may also be coupled, through switch 174, to one or more of the acoustic sensors. The data acquisition system 190 acquires, performs A/D conversion, produces and saves the digital pressure data, and/or acoustic data.

The RF circuit 110 includes an antenna 151, a transceiver 153, memory 155, a processor 157 and a collection of one or more transmit amplifiers and receive amplifiers (shown collectively as amplifiers 159). For example, the processor 157 may be similar to the microcontroller 160. Optionally, the transceiver 151 may be provided as a single component or a separate transmitter and a separate receiver. The one or more transmit amplifiers 159 are configured to be selectively connected between an output of the transmitter of the transceiver 153 and the antenna 151. The one or more receive amplifiers 159 are configured to be selectively connected between the antenna 151 and an input of the receiver of the transceiver 153.

As explained herein, the transmitter and receiver of the transceiver 153 exhibit certain power and sensitivity limits based on the components and design of a particular implementation, without the addition of transmit or receive amplifiers 159. For example, a transmitter of the transceiver 153 may be able to transmit at a power level up to −10 0dBm when operated alone without the addition of a separate transmit amplifier 159. One or more transmit amplifiers 159 may be provided to be selectively connected between the output of the transmitter in the antenna to boost the transmit power, such as up to 10 dBm. As another example, the receiver of the transceiver 153 may exhibit a receive sensitivity down to −85 dBm when operated alone without the addition of a separate receive amplifier 159. One or more receive amplifiers 159 may be provided to be selectively connected between the antenna 151 and the input of the receiver of the transceiver 153 to boost the receive sensitivity, such as down to −100 dBm.

As explained herein, the transmitter of the transceiver 153 transmits advertisement notices arranged in complexes, followed by idle states in accordance with an advertisement interval. The receiver of the transceiver 153 performs scan operations, during a receive window, to scan for connection requests. The scan operation, during an individual receive window, may be performed during the same period of time as transmission of the advertisement notices over corresponding advertisement channels. Optionally, the receive window and scan operation may continue after completion of transmission of the advertisement notices. Hence, the scan operation and receive window may temporarily align with the complex of advertisement notices and/or extend beyond the complex of advertisement notices into the idle state of the advertisement interval.

The RF circuit 110 is configured to handle and/or manage the bi-directional communication link between the IMD 101 and the EI 201. As explained herein, the RF circuit 110 transmits, among other things, advertisement notices in accordance with one or more advertisement schedules 195. In the example of FIG. 2, the advertisement schedules 195 are stored in the memory 194. Additionally or alternatively, the advertisement schedules 195 may be stored in ROM, RAM, firmware or other memory on the RF circuit 110. As a further example, the advertisement schedules 195 may be "stored" through settings of hardware circuitry within the RF circuit 110.

The RF circuit 110 includes a receiver that scans for connection requests from the EI 201. The RF circuit 110 is controlled by the controller circuit 160 and may support one or more wireless communication protocols while communicating with the EI 201, such as Bluetooth low energy, Bluetooth, Medical Implant Communication Service (MICS), and/or the like. The RF circuit 110 may include a transmitter, receiver, and/or a transceiver. Optionally, the RF circuit 110 may be electrically coupled to an antenna (not shown). Protocol firmware may be stored in memory 194 and/or 155, which is accessed by the controller circuit 160 and/or 157. The protocol firmware provides the wireless protocol syntax for the controller circuits 160 and 157 to assemble data packets, advertisement notices, connection requests, connection responses, establish communication links 104, and/or partition data received from the EI 201.

The controller circuit 160 is coupled to the memory 194 by a suitable data/address bus 196, wherein the programmable operating parameters used by the controller circuit 160 are stored and modified, as required, in order to customize the operation of IMD 101 to suit the needs of a particular patient. The memory 194 also stores data sets (raw data, summary data, histograms, etc.), such as the IEGM data, heart sound data, pressure data, Sv02 data and the like for a desired period of time (e.g., 1 hour, 24 hours, 1 month). The memory 194 may store instructions to direct the controller circuit 160 to analyze the cardiac signals and heart sounds identify characteristics of interest and derive values for predetermined statistical parameters.

In addition, the memory 194 stores one or more advertisement schedules 195. The advertisement schedule 195 may be loaded in the memory 194 at the time of manufacture, at the time of activation, at the time of installation or throughout operation. The advertisement schedule 195 includes first and second power schemes utilized with the advertisement notices. The power schemes defines one or both of i) different first and second power levels for transmitting advertisement notices and/or ii) different first and second receive sensitivities to scan for connection requests. For example, the first power scheme may define a first transmit power level and/or a first receive sensitivity to be used by a transceiver of the RF circuit 110, while the second power scheme defines a second transmit power level and/or a second receive sensitivity.

In the example of FIG. 2, the advertisement schedule 195 includes three power schemes having corresponding transmit powers (Tx Pwr) of TP1, TP2, and TP3. The power schemes have corresponding receive sensitivities (Rx Sns)

of RS1, RS2 and RS3, and have corresponding advertisement intervals (Ad Int) of AI1, AI2, and AI3. Optionally, more or fewer power schemes may be defined. Optionally, two or more power schemes may utilize the same transmit power and same advertisement interval, but different receive sensitivities. Optionally, other power schemes may utilize the same receive sensitivities, but different transmit powers and advertisement intervals. Non-limiting examples are described herein for transmit powers, receive sensitivities and advertisement intervals.

By way of example, the first power scheme may correspond to a short range advertisement scheme, while the second power scheme may correspond to a long-range advertisement scheme. The short range advertisement scheme includes a transmit power TP1 and receive sensitivity RS1 that are relatively low, as compared to the transmit power TP2 and receive sensitivity RS2 of a long range advertisement scheme. Optionally, the first or second power schemes may be utilized after a communications session has been established. Additionally or alternatively, the third power scheme may define an advertisement scheme to be utilized after a communications session has ended. Additionally or alternatively, the third power scheme may correspond to an alternative short range advertisement scheme, alternative long-range advertisement scheme, an emergency advertisement scheme, a "low battery" condition advertisement scheme and the like.

In accordance with embodiments herein, the advertisement schedule 195 balances fast advertisement at low power and low sensitivity in conjunction with slow advertisement at high power and high sensitivity, to afford quick patient initiated CODs and to afford longer range automatic connections for remote monitoring. As explained herein, once a connection is made between the external device and the IMD, the RF circuit 110 sets the transmit power and receive sensitivity to a desired communications session level (e.g., high) for a duration of the communication session. The transmit power and receive sensitivity are set to the desired communications session level regardless of whether the connection was established using short or long range advertisement, thereby affording a desired communications distance during an active communications session. For example, if a patient wanted to initiate a remote monitoring session, the patient would hold the external device (smart phone) close to the body in order to begin the communications session in accordance with short range advertisement. Then once the connection is made, the RF circuit 110 adjusts the transmit power and receive sensitivity to a communications session level (e.g., max power settings), thereby allowing the patient to leave the external device (smart phone) on a table and go to bed on the other side of the room without experiencing any disruption of the communication session.

By varying the power and advertisement interval, the new advertisement schedule 195 has several advantages over existing schemes. First, by transmitting low power advertisements at a fast rate, the EI 201 is able to connect quickly to the IMD 101. Second, the advertisement schedule 195 reduces the total power consumed, during an advertisement interval, even though the total number of advertisement pulses increases. Third, the advertisement schedule 195 eliminates a need for a custom external activator (e.g. magnet) to be placed within close proximity of the implant to trigger faster advertisement as fast, short range advertisement is "always on". Fourth, while allowing for fast, short range connectivity, the advertisement schedule 195 still supports longer range connectivity for automatic remote monitoring.

In the foregoing example, one set of power schemes is utilized in connection with communication between the IMD 101 and any EI 201. Additionally or alternatively, one or more separate advertisement schedules 195 may be stored in the memory 194 to be used in connection with individual corresponding EIs 201. For example, when an IMD 101 initially begins communicating with a particular EI 201, the EI 201 may download a corresponding advertisement schedule 195, along with the instruction to utilize the advertisement schedule 195 until otherwise instructed. Subsequently, the IMD 101 may communicate with another EI 201 that downloads a corresponding new advertisement schedule 195, along with an instruction to utilize the new advertisement schedule 195 until otherwise instructed.

As a further example, the IMD 101 may update the advertisement schedule 195 throughout operation, such as based upon the success rate at which communications links are established, based on delays when establishing communications links and the like. For example, the IMD 101 may adjust (e.g., increase or decrease) the transmit power TP1 and/or the receive sensitivity RS1 for the first power scheme by successive increments based upon a recent success rate and/or a direction from the EI 201. As another example, the IMD 101 may adjust (e.g., increase or decrease) the advertisement interval AI1 based upon a recent success rate and/or an instruction from the EI 201.

The pacing and other operating parameters of the IMD 101 may be non-invasively programmed into the memory 194 through the RF circuit 110 in bi-directional wireless communication with the EI 201. The RF circuit 110 is controlled by the controller circuit 160 and receives data for transmission over a control line 111. The RF circuit 110 allows intra-cardiac electrograms, pressure data, acoustic data, Sv02 data, and status information relating to the operation of IMD 101 (as contained in the controller circuit 160 or memory 194) to be sent to the EI 201 through an established bi-directional communication link 104. The RF circuit 110 also allows the EI 201 to program new pacing parameters and advertisement schedules for the IMD 101.

The RF circuit 110 transmits one or more advertisement notices on one or more advertisement channels. Each advertisement channel is a point to multipoint, unidirectional, channel to carry a repeating pattern of system information messages such as network identification, allowable RF channels to establish the communication link 104, and/or the like that is included within the advertisement notice. The advertisement notice may be repeatedly transmitted after a set duration or an advertisement interval based on an advertisement schedule stored in the memory 194 until the communication link 104 is established with the EI 201.

The IMD 101 may also include a physiologic sensor 112, such as an accelerometer commonly referred to as a "rate-responsive" sensor because it is typically used to record the activity level of the patient or adjust pacing stimulation rate according to the exercise state of the patient. Optionally, the physiological sensor 112 may further be used to detect changes in cardiac output, changes in the physiological condition of the heart, or changes in activity (e.g., detecting sleep and wake states) and movement positions of the patient. While shown as being included within IMD 101, it is to be understood that the physiologic sensor 112 may also be external to the IMD 101, yet still be implanted within or carried by the patient. A common type of rate responsive sensor is an activity sensor incorporating an accelerometer or a piezoelectric crystal, which is mounted within the housing 138 of the IMD 101.

Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 101 additionally includes a battery 113, which provides operating power to all of the circuits shown. Optionally, the IMD 101 may include an impedance measuring circuit 115 which is enabled by the controller circuit 160 via a control signal 114. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 115 is advantageously coupled to the switch 174 so that impedance at any desired electrode may be will soon as the obtained.

Figure 3:
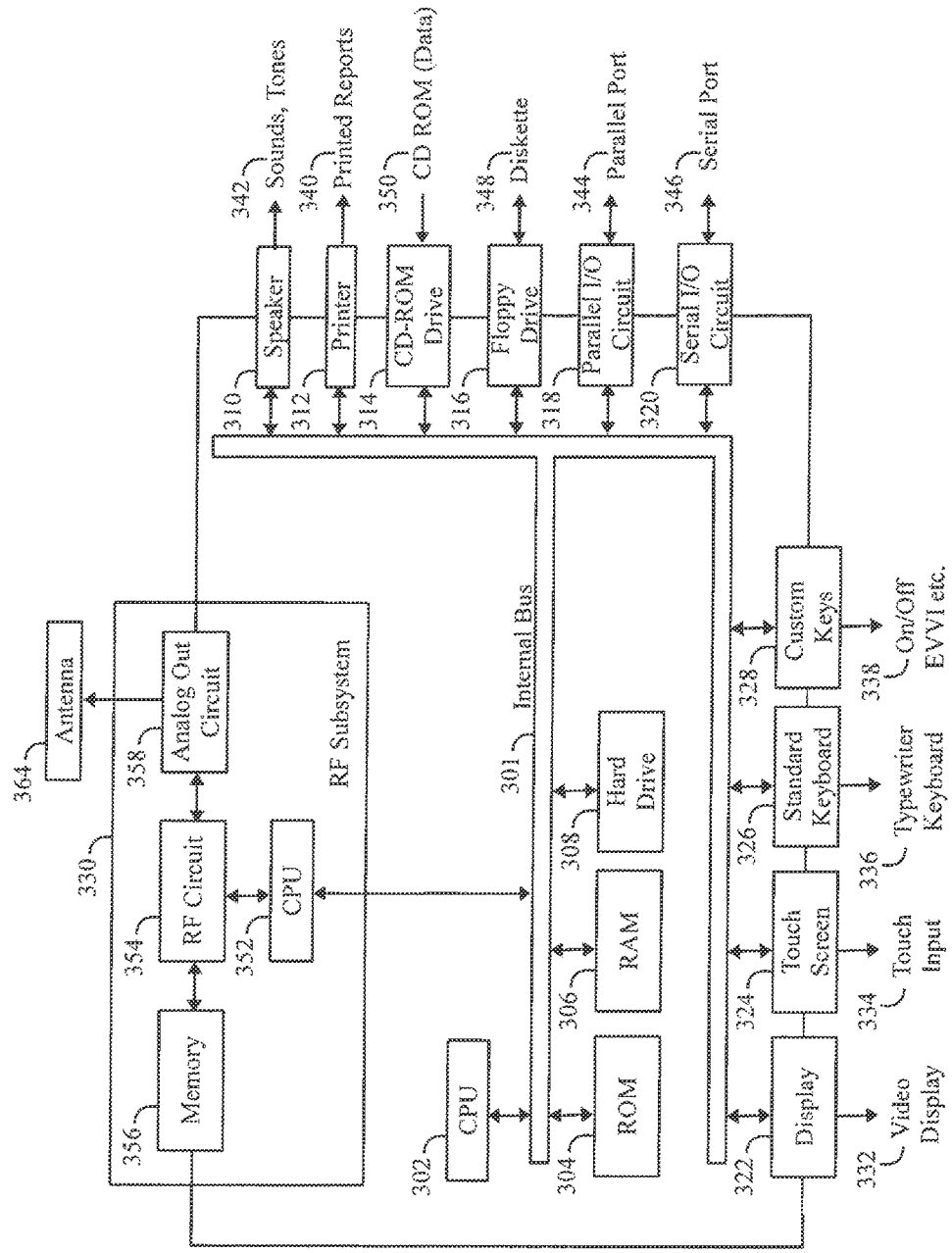
FIG. 3 illustrates a functional block diagram of the EI that is operated in accordance with embodiments herein.

FIG. 3 illustrates a functional block diagram of the EI 201 that is operated in accordance with embodiments herein. The EI 201 may be a workstation, a portable computer, a tablet computer, a smart watch, an IMD programmer, a PDA, a cell phone and/or the like. The EI 201 may include an internal bus 301 that may connect/interface with a Central Processing Unit ("CPU") 302, ROM 304, RAM 306, a hard drive 308, a speaker 310, a printer 312, a CD-ROM drive 314, a floppy drive 316, a parallel I/O circuit 318, a serial I/O circuit 320, the display 322, a touchscreen 324, a standard keyboard 326, custom keys 328, and an RF subsystem 330. The internal bus 301 is an address/data bus that transfers information between the various components described herein. The hard drive 308 may store operational programs as well as data, such as stimulation waveform templates and detection thresholds.

The CPU 302 typically includes a microprocessor, a micro-controller, or equivalent control circuitry, designed specifically to control interfacing with the EI 201 and with the IMD 101. The CPU 302 may include RAM or ROM memory, logic and timing circuitry, state machine circuitry, and I/O circuitry to interface with the IMD 101. The display 322 (e.g., may be connected to the video display 332). The display 322 displays various information related to the processes described herein. The touchscreen 324 may display graphic information relating to the IMD 101 and include a graphical user interface. The graphical user interface may include graphical icons, scroll bars, buttons, and the like which may receive or detect user or touch inputs 334 for the EI 201 when selections are made by the user. Optionally the touchscreen 324 may be integrated with the display 322. The keyboard 326 (e.g., a typewriter keyboard 336) allows the user to enter data to the displayed fields, as well as interface with the RF subsystem 330. Furthermore, custom keys 328 turn on/off 338 (e.g., EVVI) the EI 201. The printer 312 prints copies of reports 340 for a physician to review or to be placed in a patient file, and the speaker 310 provides an audible warning (e.g., sounds and tones 342) to the user. The parallel I/O circuit 318 interfaces with a parallel port 344. The serial 1/O circuit 320 interfaces with a serial port 346. The floppy drive 316 accepts diskettes 348. Optionally, the serial I/O port may be coupled to a USB port or other interface capable of communicating with a USB device such as a memory stick. The CD-ROM drive 314 accepts CD ROMs 350. One or more scanning schedules are stored in the RAM 306, ROM 304, on a CD ROM 350, or elsewhere.

The RF subsystem 330 includes a central processing unit (CPU) 352 in electrical communication with an RF circuit 354, which may communicate with both the memory 356 and an analog out circuit 358. The analog out circuit 358 includes communication circuits to communicate with an antenna 364. The EI 201 may wirelessly communicate with the IMD 101 and utilize protocols, such as Bluetooth, Bluetooth low energy, MICS, and/or the like. For example, the memory 356, ROM 304, and/or RAM 306 may include Protocol firmware, which is accessed by the CPU 352 and/or 302. The protocol firmware provides the wireless protocol syntax for the CPU 352, 302, 157, and/or 160 to assemble data packets, establish communication links 104, and/or partition data received from the IMD 101. The RF subsystem 330 and CPU 352 enter scanning states and establish communication sessions as described herein.

Advertising Power Management

Figure 4:
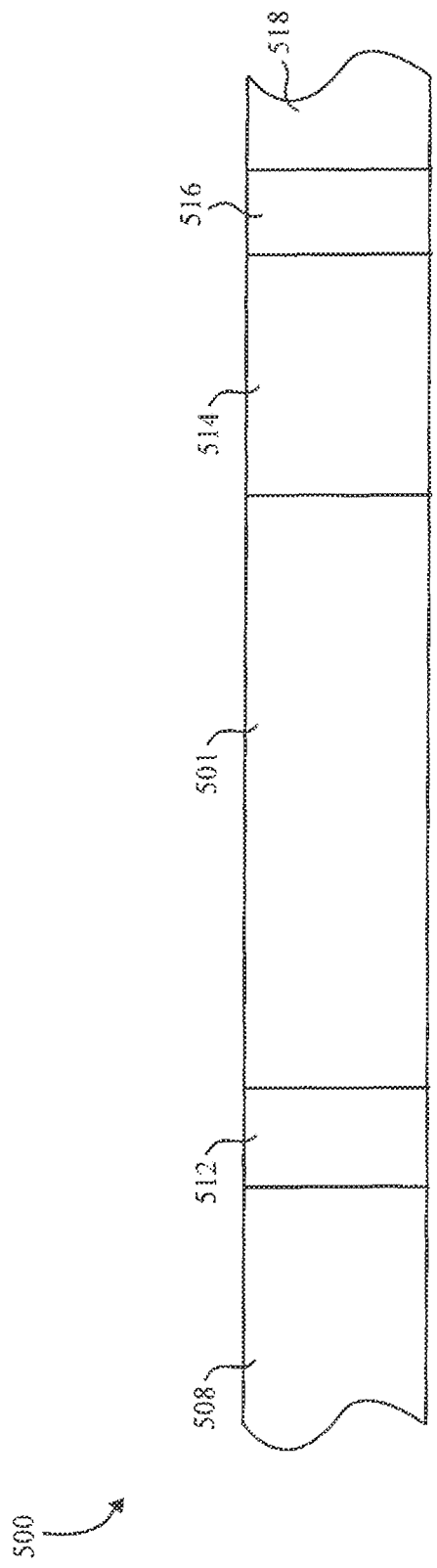
FIG. 4 is a timing diagram for establishing the wireless bi-directional communication link between the IMD and the EI in accordance with embodiments herein.

FIG. 4 is a timing diagram 500 for establishing the wireless bi-directional communication link 104 between the IMD 101 and the EI 201. The timing diagram 500 includes first and second communication sessions 501 and 518. During the communication sessions 501, 518 the IMD 101 and the EI 201 may exchange data packets along the wireless bi-directional communication link 104. Each of the communication sessions 501, 518 are established by the IMD 101 and the EI 201 based on an advertisement state 508, 514 defined as described herein. The advertisement states 508, 514 are followed by an exchange of connection requests and connection responses which occurs during an interval generally referred to as an establishment state 512, 516.

During the advertisement state 508 and 514, the IMD 101 may periodically transmit data packets corresponding to advertisement notices along one or more advertisement channels. For example, the advertisement notices may be repeated, at intervals defined by an advertisement schedule. The advertisement notices may include frequency synchronization information utilized to form the communication link 104, address information of the IMD 101, address information of the EI 201, pairing and/or bonding information, manufacturer specific alerts, and/or the like to form the wireless bi-directional communication link 104. The information contained in the advertisement notice may be utilized by the EI 201 to establish the wireless bi-directional communication link.

During scanning operations, the EI 201 scans for advertisement notices over one or more advertisement channels. When an advertisement notice is detected, the EI 201 obtains relevant information from the advertisement notice and based thereon, transmits a connection request to the IMD 101 to establish the wireless bi-directional communication link 104. During the scanning operation, the EI 201 monitors one or more advertisement channels during a scanning window for the advertisement notice. The scanning window corresponds to a length of time the EI 201 may listen to the one or more advertisement channels for the advertisement notice. When the EI 201 receives the advertisement notice, the EI 201 may transmit a data packet representing a connection request along the advertisement channel of the received advertisement notice to the IMD 101. The connection request may include instructions, such as a frequency of the data channel for the wireless bi-directional communication link 104. When the IMD 101 receives and confirms the connection request, the IMD 101 may monitor the data channel identified within the connection request for further instructions from the EI 201, thereby establishing the bi-directional communication link 104 starting the communication sessions 501, 518. Additionally or alternatively, the EI 201 and the IMD 101 may initiate a pairing and/or bonding procedure as described in in U.S. patent application Ser. No. 14/091,809, entitled, "SYSTEM AND METHODS FOR ESTABLISHING A COMMUNICATION SESSION BETWEEN AN IMPLANTABLE MEDICAL DEVICE AND AN EXTERNAL DEVICE," which is expressly incorporated herein by reference.

Figure 5:
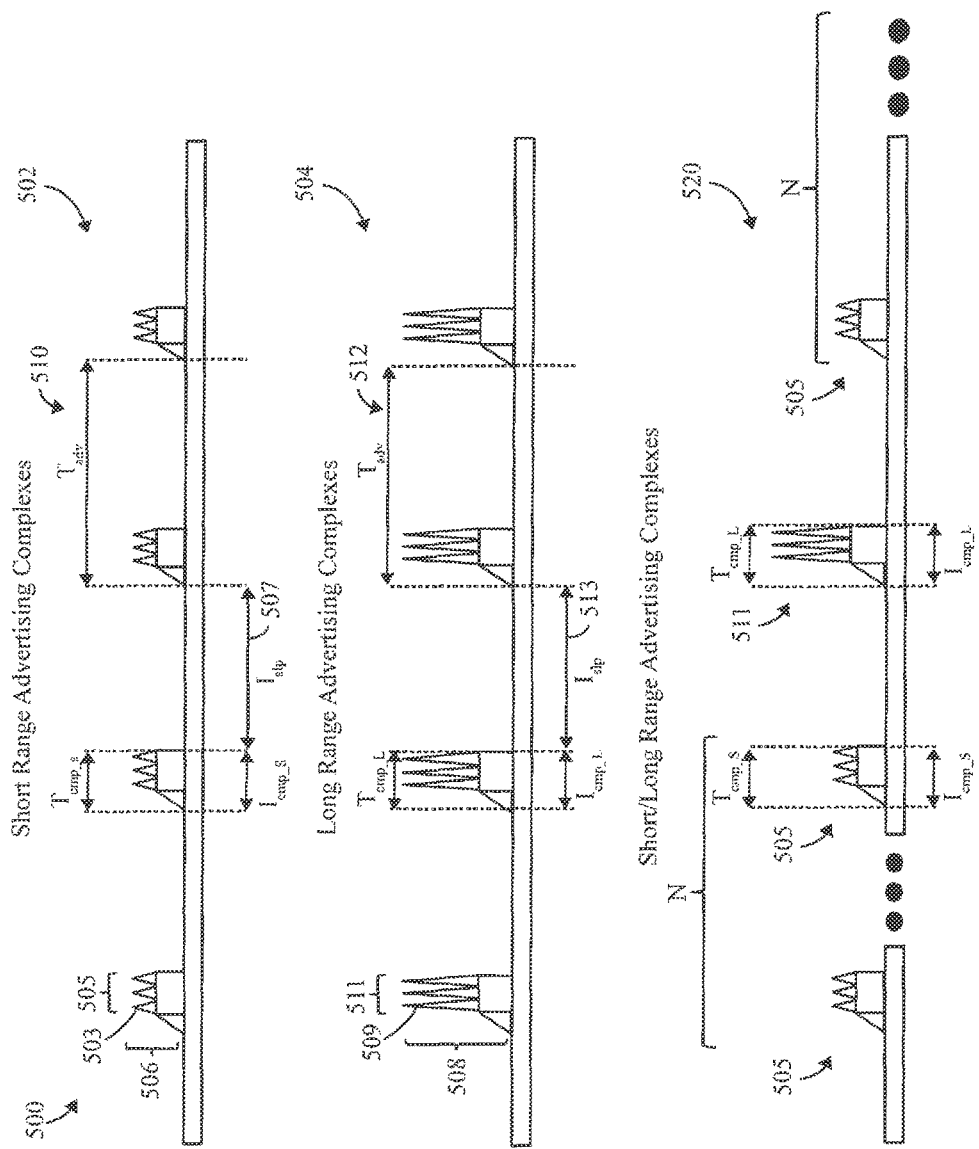
FIG. 5 illustrates an example of an advertisement schedule implemented in accordance with an embodiment herein.

FIG. 5 illustrates an example of an advertisement schedule implemented in accordance with an embodiment herein. The advertisement schedule 500 includes first and second power schemes 502, 504 that are to be utilized with different advertisement notices. The first power scheme 502 defines a first power level 506 to be used by the IMD for transmitting advertisement notices 503 and/or a first received sensitivity to be used by the IMD when scanning for connection requests. The first power scheme 502 also defines a first advertisement interval 510 between consecutive advertisement notices. The second power scheme 504 defines a second power level 508 to be used by the IMD for transmitting advertisement notices 509 and/or a second received sensitivity to be used by the IMD when scanning for connection requests. The second power scheme 504 also defines a second advertisement interval 512 between consecutive advertisement notices.

The advertisement intervals 510, 512 have corresponding different advertisement periods $T_{adv}$. In accordance with the first power scheme 502, the advertisement notices 503 are arranged in a short range advertisement complex 505 of three advertisement notices 503. The complex 505 of advertisement notices 503 are transmitted over a short range advertisement complex time $T_{cmp\_S}$ followed by an idle time 507. In accordance with the second power scheme 504, the advertisement notices 509 are arranged in a long range advertisement complex 511 of three advertisement notices 509. The complex 511 of advertisement notices 509 are transmitted over a long range advertisement complex time $T_{cmp\_L}$ followed by an idle time for a remainder of the advertisement interval 512. During the short range advertisement complex 505, the advertisement operation draws a current demand $I_{cmp\_S}$. During the long range advertisement complex 511, the advertisement operation draws a current demand $I_{cmp\_L}$. During the advertisement intervals 510, 512, after completion of transmission of the corresponding advertisement notices and receive operations listening for connection requests, the RF circuit 110 enters the idle or sleep state, during which a sleep current $I_{slp}$ is drawn from the battery.

In the example of FIG. 5, the advertisement schedule 500 is shown to transmit three advertisement notices 503, 509 during one complex 505, 511 because the IMD is configured to advertise over three separate channels. Optionally, more or fewer advertisement notices and advertisement channels may be utilized. For example, the complex 505 and/or 511 may include a single advertisement notice, two advertisement notices or more than three advertisement notices. Also, a single complex 505, 511 is transmitted at a beginning of the advertisement interval 510, 512, followed by an idle state 507, 513 for the remainder. Optionally, more than one complex 505, 511 of advertisement notices 503, 509 may be transmitted during one corresponding advertisement interval 510, 512.

The third power scheme 520 merges the first and second power schemes 502, 504 with one another such that complexes 505, 511 are time interleaved with one another as indicated along the timeline for the power scheme 520. The advertisement schedule 500 includes a series of N short range advertisement complexes 505 (e.g., where N is greater than or equal to 1) that are transmitted successively with one another, between consecutive long range advertisement complexes 511. The series N of short range advertisement complexes 505 are bordered by a single long range advertisement complex 511. After the single long range advertisement complex 511, another series of N short range advertisement complexes 505 are transmitted successively with one another and in an un-interrupted manner. The power scheme 520 repeats the short series and single long range advertisement complexes 505, 511 with corresponding first and second power schemes over time.

Next, a discussion is provided concerning certain technical details that may be considered in connection with defining advertisement schedules in accordance with embodiments herein. The following Table 1 provides descriptions and units for terminology used in FIG. 5 and elsewhere herein.

TABLE 1

| Terminology | Units | Description |
| --- | --- | --- |
| $T_{adv}$ | s | Advertisement Period |
| N | counts | Number of Short Range Advertisements before a Long Range Advertisement |
| $T_{cmp\_S}$ | ms | Short Range Advertisement Complex Time |
| $T_{cmp\_L}$ | ms | Long Range Advertisement Complex Time |
| $I_{cmp\_S}$ | uA | Short Range Advertisement Complex Current |
| $I_{cmp\_L}$ | uA | Long Range Advertisement Complex Current |
| $I_{slp}$ | nA | Sleep Current |
| $I_{avg}$ | uA | Average Current |

Various embodiments may utilize different advertisement schedules that will yield corresponding different power savings as compared to continuous long range advertisement alone. It is recognized that different wireless communications chipsets may be utilized for the RF circuit 110 which will exhibit different corresponding power/sensitivity capabilities and demands. As one example, an IMD may be configured with an RF circuit that has one or more amplifiers that provide a maximum RF power of 5 dBm (decibel milliwatts) to support a maximum communications distance of approximately 5 meters or slightly more. The maximum communications distance may be limited by the uplink (e.g., implant to external), as per the system link budget. The system link budget determines how effective two devices can communicate with each other, with respect to various signal limitations and losses, such as distance in air, environmental interference, antenna gain, output power, and receive sensitivity. After accounting for the various losses, the remaining signal is considered the link margin; if the link margin is negative, then a communications link cannot be established. In general, due to limited battery and power saving requirements, an implanted device does not transmit at full power, and so limits the link margin in the uplink direction.

Alternatively, when the communications distance is limited to short ranged (e.g., in terms of a patient's arm length and in connection with a handheld device), the communications distance is substantially shorter than the maximum capability of the RF circuit. For example, the short range distance may be defined to be up to 1 meter (e.g., maximum arm length) and the transceiver of the RF circuit may be able to support communications up to 1 m with an RF power of −10 dBm without use of a separate amplifier. In the present example, the RF circuit would exhibit a link margin of approximately 15 dB (5 dBm−(−10 dBm)), meaning the difference between high power and lower power advertisements could be up to 15 dB. Table 2 illustrates an example of advertisement complex characteristics of various power settings for an RF circuit.

TABLE 2

| Output Power (dBm) | Advertisement Current (uA) | Advertisement Time (ms) |
|---|---|---|
| 5 | 1500 | 7.000 |
| 0 | 800 | 7.200 |
| −10 | 600 | 7.500 |

For a standard advertisement schedule, the following Equation #1 may be used to calculate the average BLE current utilized for 1 advertisement every $T_{adv}$ seconds in accordance with a BLE protocol:

$$Iavg = \left(\frac{Tcmp}{Tadv} \times Icmp\right) + \left(\frac{Tadv - Tcmp}{Tadv} \times Islp\right) \quad \text{Equation 1}$$

By way of example, during normal advertising operation over time, an RF circuit may generally consume up to 1 uA on average. When select values are used for the range complex current $I_{cmp}$, the advertisement interval $T_{adv}$ and the sleep current $I_{slp}$, the previous Equation #1 yields the following values in Table 3 for average current $I_{avg}$. Average current values are shown for long, nominal, and short range advertisement complexes.

TABLE 3

| Output Power (dBm) | Average Current (uA) |
|---|---|
| 5 | 1.900 |
| 0 | 1.400 |
| −10 | 1.000 |

As another example, the following Equation #2 may be utilized to calculate the average current for 1 short range advertisement every $T_{adv}$ seconds and 1 long range advertisement after every N short range advertisements, where the variables are described above in Table 1.

$$Iavg = \frac{\left\{\left(\frac{Tcmp\_S}{Tadv} \times Icmp\_S\right) + \left[\left(\frac{Tadv - Tcmp\_S}{Tadv}\right) \times Islp\right]\right\} \times N + \left\{\left[\frac{Tcmp\_L}{Tabv} \times Icmp\_L\right] + \left[\left(\frac{Tadv - Tcmp\_L}{Tadv}\right) \times Islp\right]\right\}}{N+1}$$

Table 4 below shows examples of average current and savings for various short/long range advertisement ratios N, when the advertisement period $T_{adv}$ is assumed to be 5 seconds. In Table 4, it is assumed that one long range advertisement complex is transmitted for every N short range advertisement complexes. In the example, where N=0, every advertisement represents a long range advertisement, while in the example where N=∞, every advertisement represents a short range advertisement. The current (I) savings is relative to only using long range advertisements (e.g., when N=0).

TABLE 4

| N | Ratio LR/SR | Seconds | Minutes | Iavg (uA) | I Savings |
|---|---|---|---|---|---|
| 0 | 100.0% | 5 | 0.08 | 1.900 | 0.0% |
| 1 | 50.0% | 10 | 0.17 | 1.400 | 20.0% |
| 3 | 25.0% | 20 | 0.33 | 1.200 | 35.0% |
| 4 | 20.0% | 25 | 0.42 | 1.150 | 37.0% |
| 23 | 4.2% | 120 | 2.00 | 1.050 | 45.0% |
| ∞ | 0.0% | N/A | N/A | 1.000 | 47.0% |

Table 4 shows that at a minimum, a 20.0% current reduction can be attained when alternating long and short advertisements 1 for 1. As another example, when the ratio of long to short range advertisements is 1:4 (20%), the current savings is approximate 37% as compared to using only long range advertisements. A theoretical maximum reduction of 47.0% could be achieved by using all short range advertisement complexes. As a further example, using the data from Table 2, the IMD may only advertise using long range advertisements every 10 seconds and still meet a 1 uA average advertisement current limit.

Table 5 shows example advertisement periods for merging short and long range advertisements. Note that the IMD may advertise twice as often if one long range advertisement complex is transmitted each hour. The examples of Table 5 would exhibit potential IMD longevity gains while also extending the advertisement period $T_{adv}$.

TABLE 5

| | | LR Adv Every X | | | |
|---|---|---|---|---|---|
| $T_{adv}$ (s) | N | Ratio LR/SR | Seconds | Minutes | $I_{avg}$ (uA) |
| 5 | 719 | 0.1% | 3600 | 60.00 | 1.000 |
| 6 | 4 | 20.0% | 30 | 0.50 | 0.990 |
| 8 | 1 | 50.0% | 16 | 0.27 | 0.900 |

Based on Equations #1 and #2 and the examples in Tables 1-5, various advertising schedules may be defined based on the capabilities of a particular RF circuit and the IMD's battery capacity.

Figure 6:
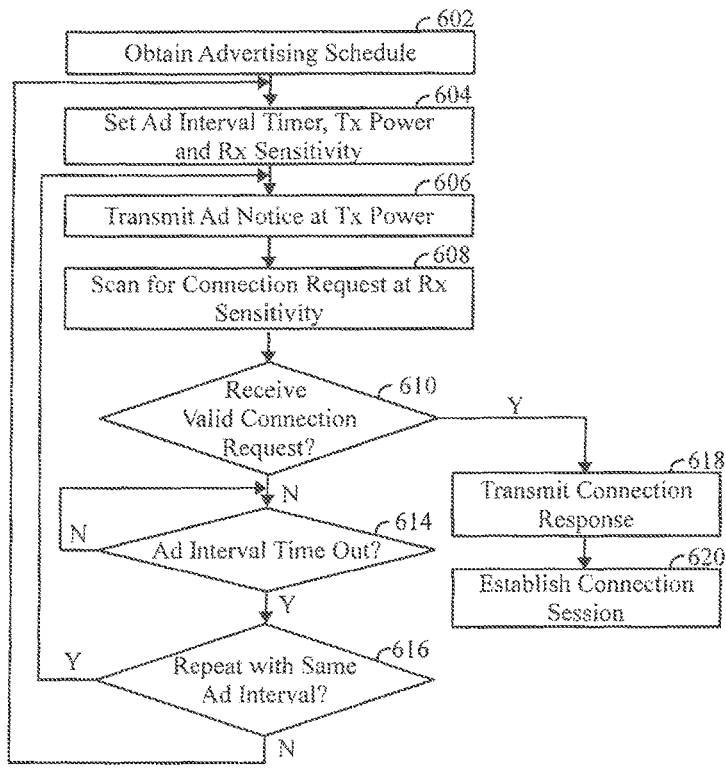
FIG. 6 illustrates a flowchart for a method performed by the IMD during the advertisement state to implement a given advertisement schedule in accordance with embodiments herein.

FIG. 6 illustrates a flowchart for a method performed by the IMD 101 during the advertisement state to implement a given advertisement schedule. The method may be implemented as a software algorithm, package, or system that directs one or more hardware circuits or circuitry to perform the actions described herein. For example, the operations of the method may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the IMD.

At 602, the processor of the IMD 101 obtains an advertisement schedule stored in memory. The advertisement schedule includes at least two power schemes that define short and long-range advertising schemes to be iteratively repeated in connection with different advertisement notices. By way of example, the Equations #1 and #2 and Tables 1-5 may be utilized to define first, second and third power schemes (e.g. AI1-3, TP1-3, RS1-3 as shown in FIG. 2). At 604, based on a power scheme, the processor sets an advertisement interval timer to an advertisement interval based on the advertisement schedule. At 604, the processor also sets the transmit power used by the transmitter when transmitting advertisement pulses and the receive sensitivity to be used by the receiver when scanning for connection request. For example, with reference to FIG. 2, the processor may set the advertisement interval timer to correspond to the advertisement interval AI1, the transmit power at TP1 and the receive sensitivity at RS1. When the transmit power (e.g., TP1) is low and can be satisfied by the transmitter alone (e.g., unamplified), an unamplified output of the transmitter is directly connected to the antenna and one or more amplifiers are bypassed. Alternatively, when the transmit power (e.g., TP3) is high and cannot be satisfied by the transmitter alone, an output of the amplifier is connected to an amplifier which provides an amplified output connected to the antenna.

Optionally, when the receive sensitivity (e.g., RS1) is low and can be satisfied by a receiver alone (e.g., unamplified), the antenna is connected directly to the input of the receiver as an un-amplified input and one or more receive amplifiers are bypassed. Alternatively, when the receive sensitivity (e.g., RS3) is high and cannot be satisfied by the receiver alone, the antenna is connected to a receive amplifier and an output of the receive amplifier is in turn connected to the input of the receiver.

At 606, the transmitter of the IMD 101 (e.g., RF circuit 110) transmits a complex of advertisement notices utilizing the programmed transmit power (e.g., TP1). At 608, a receiver within the IMD 101 (e.g., RF circuit 110) scans one or more channels for a connection request utilizing the programmed receive sensitivity (RS1). At 610, the processor of the IMD determines whether a valid incoming connection request has been received. For example, when a connection request is received, the content of the connection request is analyzed by the processor to determine whether the connection request is directed to the IMD 101 and has been transmitted from an authorized EI 201. For example, connection requests may be transmitted by various wireless devices. The IMD 101 may receive such connection requests even though various connection requests are not directed to the IMD 101, nor transmitted from an authorized EI 201. As one example, a valid connection request may include identification information corresponding to the IMD 101. For example, when the IMD 101 conveys an advertisement notice, the advertisement notice may include a serial number or other identification information unique to the IMD 101. An authorized EI 201, upon receiving an advertisement notice, returns the serial number and/or other identification information in a connection request. At 610, the IMD 101 analyzes the content of incoming connection request for the serial number and/or other identification information originally transmitted from the IMD 101 in advertisement notice.

Optionally, alternative information may be included in advertisement notice and connection request, and alternative types of analysis may be performed to validate incoming connection request, based on a corresponding protocol.

At 610, when a valid connection request is received, flow branches to 618. At 618, the advertisement state is terminated and an establishing state is initiated in connection with establishing a communication session. At 618, the transmitter of the IMD 101 transmits a connection response. At 620, the IMD 101 and the EI 201 establish a communications session.

Alternatively, at 610, when no connection request is received or an invalid connection request is received, flow continues to 614. At 614, the processor of the IMD waits for the advertisement interval timer to time out. At 614, when the interval timer times out, flow continues to 616. At 616, the processor of the IMD determines whether to repeat another advertisement operation using the same advertisement interval. When the same advertisement interval is to be repeated for the next advertisement notice, flow returns to 606. Otherwise, flow returns to 604 where a new advertisement interval is set from the advertisement schedule.

For example, the advertisement schedule indicates that N short range advertisement complexes should be transmitted in succession before switching to a long range advertisement complex. Accordingly, the operations at 606-616 may be repeated N times while utilizing the short range advertisement complex (e.g., the short range power level, receive sensitivity and advertisement interval). After N short range advertisement complexes, flow moves from 616 back to 604, where the advertisement interval timer, transmit power and receive sensitivity are reset. For example, the advertisement schedule may indicate that one long range advertisement complex should be transmitted. Accordingly, the operations at 606-616 are performed once while utilizing the long range advertisement complex (e.g., the long range power level, receive sensitivity and advertisement interval). Thereafter, flow moves from 616 back to 604 again, and the advertisement schedule re-sets the advertisement interval, transmit power and receive sensitivity to the short range advertisement complex.

Figure 7:
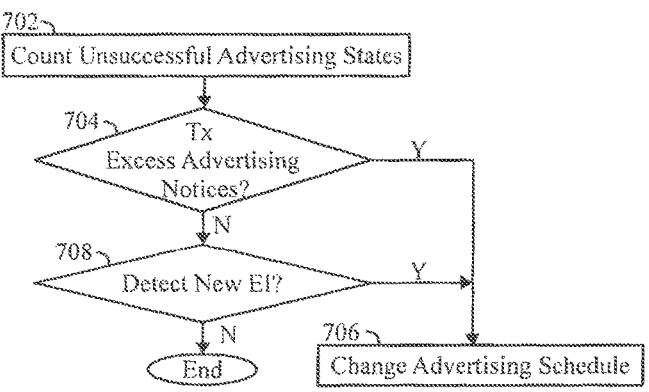
FIG. 7 illustrates a process for changing the advertisement schedule in accordance with embodiments herein.

FIG. 7 illustrates a process for changing the advertisement schedule in accordance with an embodiment. At 702, the processor of the IMD tracks the number of advertisement states that have occurred without a successful connection. At 704, the processor of the IMD 101 determines whether the IMD 101 has transmits an unduly large number of advertisement notices over an excessive number of advertisement states without connecting with an EI 201. As explained herein, the transmitter of the IMD 101 repeats the transmitting operation over one or more advertisement states, when a connection request from the IE is not detected. When the number of unsuccessful advertisement states exceeds a predetermined threshold, flow moves to 706. At 706, the processor of the IMD 101 changes the advertisement schedule. For example, the advertisement schedule may be switched from utilizing short range advertisement complexes to long-range advertisement complexes. Additionally or alternatively, the advertisement interval may remain at a relatively fast rate (e.g., associated with short range advertisement complexes), but with an increase in transmit power and receive sensitivity (e.g., associated with long-range advertisement complexes). For example, the advertisement schedule may be changed by at least one of i) changing the transmit power, ii) changing the receive sensitivity, iii) changing the number of complexes transmitted during one advertisement interval and/or iv) changing the advertisement interval.

At 708, the processor of the IMD 101, detects when a new EI is communicating with the IMD 101. When a new EI is detected, flow moves to 706 and the processor of the IMD 101 may change from a long range advertisement complex associated with a first EI, to a short range advertisement complex associated with a second EI. It should be recognized that either advertisement complex may be useful with various different EI, however, different advertisement complexes may be tailored to correspond to the scanning schedules associated with individual EI. Accordingly, the processor of the IMD 101 may change the advertisement schedule based upon different EI that are communicating there with. For example, the IMD 101 may be configured to communicate with multiple EI. Each EI may have a different scanning schedule, power requirements and the like.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method of operating an implantable medical device (IMD) for conducting communications, after implantation within a patient, with a device external to the patient, the method comprising:
   operating wireless communication circuitry of the IMD to provide advertising notices according to a wireless communication protocol for establishment of one or more wireless communication sessions between the IMD and the device external to the patient, wherein (1) the operating comprising providing advertising notices according to first and second connection schemes, (2) the first connection scheme provides advertising notices according to a first frequency and the second connection scheme provides advertising notices according to a second frequency, (3) the first frequency is greater than the second frequency to provide lesser connection latency according to the first connection scheme compared to connection latency of the second connection scheme, (4) the operating provides advertising notices according to the first connection scheme at a lower transmit power than advertising notices according to the second connection scheme, and (5) the operating employs the first and second connection schemes for providing advertising notices according to a schedule;
   receiving a request from the device external to the patient to establish a communication session with the IMD in response to device external to the patient receiving an advertising notice from the IMD;
   establishing a communication session with the device external to the patient to communicate IMD data with the device external to the patient; and
   communication IMD data with the device external to the patient.

2. The method of claim 1, wherein the first connection scheme defines a short range advertisement scheme having a first transmit power level configured to communicate with an external device up to 1 meter from the IMD.

3. The method of claim 2, wherein the first transmit power level is no more than −5 dBm.

4. The method of claim 1, wherein the second connection scheme defines a long range advertisement scheme having a second transmit power level configured to communicate with an external device that is greater than 1 meter away from the IMD.

5. The method of claim 4, wherein the second transmit power level is configured to communicate with an external device that is up to 5 meters away from the IMD.

6. The method of claim 4, wherein the second transmit power level is at least 3 dBm.

7. The method of claim 1, wherein the schedule repeats the first connection scheme N times before repeating the second connection scheme, where N is greater than or equal to 1.

8. The method of claim 1, wherein the first and second connection schemes corresponding to short and long range connection schemes, and wherein the schedule merges the short and long range connection schemes in a ratio LR/SR of no more than 50.0%, where LR corresponds to a number of long range advertisement complexes transmitted during a predetermined period of time and SR corresponds to a number of short range advertisement complexes transmitted during the predetermined period of time.

9. The method of claim 1, further comprising counting a number of unsuccessful advertisement states and based thereon, changing from the first power scheme.

10. The method of claim 1, further comprising determining when a connection request is received from the device external to the patient in connection with one of the advertisement notices.

11. An implantable medical device (IMD) for implant within a patient, comprising:
   a battery for powering the IMD;
   circuitry for conducting medical operations;
   circuitry for conducting wireless communication with a device external to the patient after implant;
   memory for storing data and programmable instructions of the IMD;
   a processor for controlling operations of the IMD, wherein (1) the processor is configured to operate the wireless communication circuitry of the IMD to provide advertising notices according to a wireless communication protocol for establishment of one or more wireless communication sessions between the IMD and the device external to the patient according to first and second connection schemes, (2) the first connection scheme provides advertising notices according to a first frequency and the second connection scheme provides advertising notices according to a second frequency, (3) the first frequency is greater than the second frequency to provide lesser connection latency according to the first connection scheme compared to connection latency of the second connection scheme, (4) the processor is configured to operate the wireless communication circuitry to provide advertising notices according to the first connection scheme at a lower transmit power than advertising notices according to the second connection scheme, and (5) the processor is configured to employ the first and second connection schemes for advertising notices according to a schedule.

12. The IMD of claim 11, wherein, based on the connection power scheme, the processor is configured to define a short range advertisement scheme having a first transmit power level and a first receive sensitivity configured to communicate with an external device up to 1 meter from the IMD.

13. The IMD of claim 12, wherein the processor is configured to set the first transmit power level of the transmitter to no more than −5 dBm.

14. The IMD of claim 11, wherein, based on the second connection scheme, the processor is configured to define a long range advertisement scheme having a second transmit power level and a second receive sensitivity configured to communicate with an external device that is great than 1 meter away from the IMD.

15. The IMD of claim 14, wherein the processor is configured to set the second transmit power level and second receive sensitivity to communicate with an external device that is up to 5 meters away from the IMD.

16. The IMD of claim 14, wherein the processor is configured to set the second transmit power level to at least 3 dBm.

17. The IMD of claim 11, wherein, based on the advertisement schedule, the processor is configured to repeat the first connection scheme N times before repeating the second power scheme, where N is greater than 1.

18. The IMD of claim 11, wherein the first and second connection schemes corresponding to short and long range advertisement schemes, and wherein the advertisement schedule merges the short and long range connection schemes in a ratio LR/SR of no more than 50.0%, where LR corresponds to a number of long range advertisement complexes transmitted during a predetermined period of time and SR corresponds to a number of short range advertisement complexes transmitted during the predetermined period of time.

19. The IMD of claim 11, wherein the first connection scheme is adapted to communicate IMD data with the device external to the patient according to an on demand mode of operation and the second connection scheme is adapted to communicate IMD data according to a regular schedule.

20. The IMD of claim 11, wherein the IMD data comprises patient physiological data sensed by the IMD after implant.

* * * * *